(12) United States Patent
Dorrer et al.

(10) Patent No.: US 10,160,943 B2
(45) Date of Patent: Dec. 25, 2018

(54) METHOD AND MICROFLUIDIC SYSTEM FOR PROCESSING ORGANIC CELLS AND MANUFACTURING METHOD FOR PRODUCING A MICROFLUIDIC SYSTEM FOR PROCESSING ORGANIC CELLS

(71) Applicant: Robert Bosch GmbH, Stuttgart (DE)

(72) Inventors: Christian Dorrer, Stuttgart (DE); Bernd Faltin, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 14/691,752

(22) Filed: Apr. 21, 2015

(65) Prior Publication Data
US 2015/0307826 A1  Oct. 29, 2015

(30) Foreign Application Priority Data

Apr. 25, 2014  (DE) .................. 10 2014 207 775

(51) Int. Cl.
| | |
|---|---|
| *C12M 3/06* | (2006.01) |
| *C12M 1/00* | (2006.01) |
| *C12M 1/12* | (2006.01) |
| *C12N 1/06* | (2006.01) |

(Continued)

(52) U.S. Cl.
CPC ....... *C12M 23/16* (2013.01); *B01L 3/502753* (2013.01); *C12M 23/02* (2013.01); *C12M 25/16* (2013.01); *C12M 29/04* (2013.01); *C12M 47/02* (2013.01); *C12N 1/06* (2013.01); *B01L 2200/0647* (2013.01); *B01L 2300/0681* (2013.01); *C12M 47/04* (2013.01); *C12M 47/06* (2013.01)

(58) Field of Classification Search
CPC .. C12N 1/06; C12N 15/1003; C12N 15/1017; C12N 1/08; B01L 2200/0647; B01L 2300/0681; B01L 3/502753; C07H 1/06; C12M 23/16; C12M 25/16; C12M 29/04; C12M 47/02; C12M 47/04
USPC .......................................... 435/306.1; 506/9
See application file for complete search history.

(56) References Cited

U.S. PATENT DOCUMENTS

| | | |
|---|---|---|
| 2008/0057505 A1 | 3/2008 | Lin et al. |
| 2010/0055766 A1 | 3/2010 | Hwang et al. |

(Continued)

FOREIGN PATENT DOCUMENTS

| | | |
|---|---|---|
| EP | 1 179 585 B1 | 7/2008 |
| EP | 2 026 074 A2 | 2/2009 |
| WO | 99/33559 A1 | 7/1999 |

*Primary Examiner* — Dennis White
*Assistant Examiner* — Bryan Kilpatrick
(74) *Attorney, Agent, or Firm* — Maginot, Moore & Beck LLP

(57) ABSTRACT

A method for processing organic cells includes providing a microfluidic system having a chamber comprising a stationary phase in the form of a plurality of microparticles. The method further includes letting a plurality of organic cells in a mobile phase into the chamber across a first opening of the microfluidic system. The method further includes accumulating the organic cells in a tapered section of the chamber that is upstream of a filter of the microfluidic system that is impermeable to the microparticles. The method further includes flushing a lysis agent into the chamber to resuspend the microparticles and the organic cells in the chamber for a disruption of the organic cells.

10 Claims, 11 Drawing Sheets

(51) Int. Cl.
*B01L 3/00* (2006.01)
*C12N 15/10* (2006.01)

(56) References Cited

U.S. PATENT DOCUMENTS

| | | | |
|---|---|---|---|
| 2010/0112576 A1* | 5/2010 | Patil | G01N 1/40 |
| | | | 435/6.11 |
| 2010/0159556 A1* | 6/2010 | Rida | B01F 13/0809 |
| | | | 435/173.7 |
| 2010/0256350 A1 | 10/2010 | Rhee et al. | |
| 2012/0135471 A1* | 5/2012 | Rothacher | C12Q 1/6806 |
| | | | 435/91.2 |

* cited by examiner

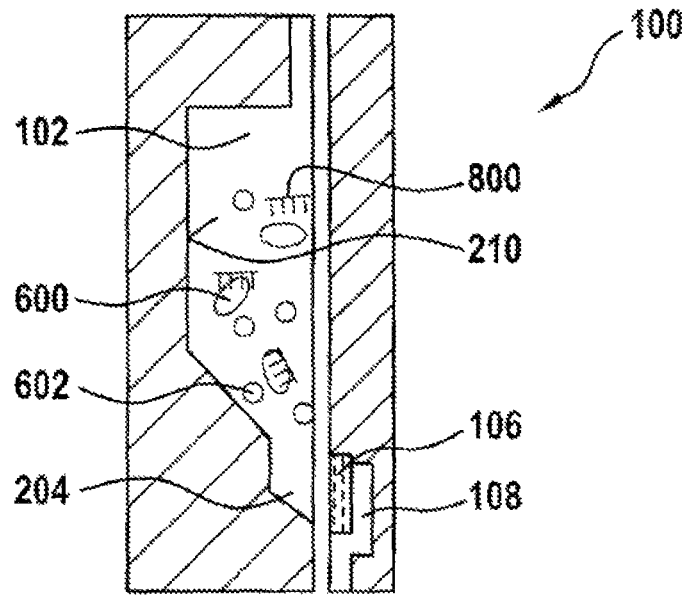
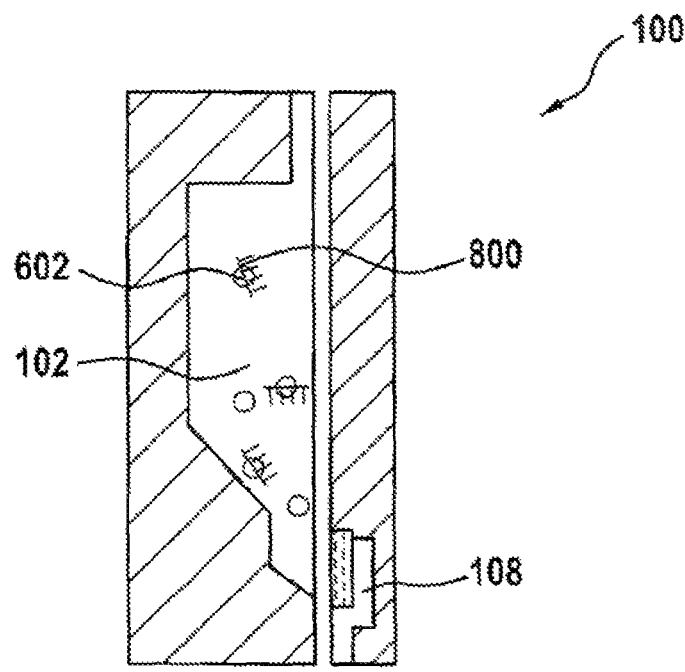

METHOD AND MICROFLUIDIC SYSTEM FOR PROCESSING ORGANIC CELLS AND MANUFACTURING METHOD FOR PRODUCING A MICROFLUIDIC SYSTEM FOR PROCESSING ORGANIC CELLS

This application claims priority under 35 U.S.C. § 119 to patent application number DE 10 2014 207 775.3, filed on Apr. 25, 2014 in Germany, the disclosure of which is incorporated herein by reference in its entirety.

BACKGROUND

The present disclosure relates to a method for processing organic cells, to a microfluidic system for processing organic cells and to a manufacturing method for producing such a microfluidic system.

In molecular diagnostics, there is often the need to detect pathogenic nucleic acids such as DNA or RNA from a sample. Pathogenic DNA or RNA refers to the DNA or RNA obtained from a pathogen, for example a virus, a bacterium or a fungus. Sample refers to the liquid to be analyzed, typically a liquid or liquefied patient sample, for example blood, urine, stool, sputum, cerebrospinal fluid, lavage fluid, a rinsed-out swab or a liquefied tissue sample. The nucleic acids are purified and subjected to an analysis by means of which the presence of particular pathogens or genes, for example resistance genes, is tested. Said analysis can, for example, be carried out by sequencing, polymerase chain reaction (PCR), real-time PCR and/or hybridization on a microarray.

A nucleic acid is often purified from a sample by disrupting or lysing the pathogens and then adsorbing the nucleic acids to a solid phase, for example a silica filter or microparticles in the form of beads. Besides chemical and enzymatic methods for lysis, there are also mechanical methods, for example using ultrasound or by grinding with beads. The goal of purification is to provide the nucleic acid in concentrated form for a subsequent amplification and/or detection. To concentrate the pathogens before the purification, the sample is, for example, centrifuged or flushed across a filter.

EP 1 179 585 B1 describes a cartridge for lysing components of a fluid sample. The cartridge has a lysis chamber having a wall to which it is possible to couple an ultrasound transducer in order to bring about a transfer of ultrasonic energy into the lysis chamber.

SUMMARY

Against this background, the approach presented here presents a method for processing organic cells, a microfluidic system using said method, and also a manufacturing method for producing a microfluidic system for processing organic cells according to the following description. Advantageous configurations are revealed by the description which follows.

A plurality of microparticles amassed to form a bed can be used for accumulating organic cells and, on the basis of a subsequent resuspension in a lysis buffer, for lysing the cells, optionally with additional mechanical agitation. In addition, the microparticles can also be used for purifying a substance, for example a DNA, released from the organic cells.

Hitherto known methods use centrifugation or fabric filters or membranes to accumulate cells from a sample. The disadvantage of a centrifugation is that it is not implementable in a microfluidic system and can therefore be integrated with difficulty into an automated procedure. When using a fabric filter or a membrane, an integration into a microfluidic system or some other automation is indeed possible, but the cells accumulated on the fabric filter are then, so to speak, "hidden" therein and can be reached with relatively great difficulty or with relatively poor efficiency for subsequent processing steps, for example a lysis. The disclosure solves these problems through the reversible packing to a filter element and resuspension of microparticles. As a result, it is possible using only one structural component to realize two opposing requirements, viz. providing an element having small pores for, for example, accumulating cells and binding nucleic acids, and washing as efficiently and completely as possible around, for example, accumulated cells or bound nucleic acids with reagents, for example lysis or wash reagents.

According to the concept proposed here, the accumulation of cells on a microparticle bed can allow a concentration of the cells which is advantageous for a later analysis. This is because it is possible, in this way, to improve a sensitivity of possible subsequent detection of, for example, pathogens in the cells. In some circumstances, it is possible, in this way, for small cell counts in a large volume to be detected in the first place. By resuspending the microparticles, the cells are released again in a smaller volume and can be advantageously effectively lysed, resulting in a concentration effect.

As a further advantage, by using the microparticles for accumulation and purification, it is possible to dispense with a membrane or a further filter for the purification. As a result, a system according to the disclosure can be configured more compactly and more cost-effectively. In a further development of the approach proposed here, it is possible by means of mechanical agitation of the microparticles during the lysis to achieve a grinding action and thus also to lyse difficult-to-lyse cells, for example fungi.

A processing method proposed here for analyzing organic cells is especially suited to an integration into a microfluidic system. The procedure is therefore amenable to automation, making it possible to save time and costs. Furthermore, the advantage of automation in a microfluidic system is that the system can be operated without special knowledge and the risk of contamination is reduced.

A method for processing organic cells is presented, wherein the method comprises the following steps:

providing a microfluidic system having a chamber comprising a stationary phase in the form of a plurality of microparticles;

letting a plurality of organic cells in a mobile phase into the chamber across a first opening of the microfluidic system;

accumulating the organic cells in a (more particularly tapered) section of the chamber that is upstream of a filter of the microfluidic system that is impermeable at least to the microparticles (in one variant, to the organic cells too); and flushing a lysis agent into the chamber in order to resuspend the microparticles and the organic cells in the chamber for a disruption of the organic cells.

In this connection, the filter of the microfluidic system is, for example, arranged between a second opening and the (more particularly tapering) section. In this respect, the filter is, in a flow direction of fluid from the second opening across the tapering section, upstream of said tapering section. In other words, the filter is, in the case of an inflow of fluid across the first opening and the tapering section of the chamber, downstream of the tapering section. Furthermore, the filter can be permeable to organic cells in one embodiment and impermeable in another embodiment.

By means of the method, the cells can be processed in the sense that nucleic acids, such as DNA or RNA, present in the cells can be made accessible to an analysis. The microfluidic system can be a layer structure having micrometer to millimeter structures for analyzing the organic cells, for example a so-called lab-on-a-chip system. In this connection, the organic cells can be present in the form of a sample in a fluid, for example a body fluid, and thus be brought to interact with the stationary phase in the chamber in such a way that, by means of the lysis agent, the cells are split open or lysed and the nucleic acids are released during this action.

For this purpose, it is possible, in one variant of the approach presented here, for the stationary phase in the form of the microparticles to be understood as a "tool" for mechanically breaking the cells open. The resuspension can be understood to mean a whirling or swirling of the organic cells and the microparticles within the chamber.

In one embodiment of the method, it is possible, in the step of flushing, for the lysis agent to be flushed in in such a way that the microparticles and the organic cells are resuspended in the chamber. This can, for example, be achieved by the lysis agent being flushed into the chamber across the second opening of the microfluidic system that is downstream of the filter. In this way, the resuspension, i.e. the whirling, of the cells and microparticles and thus the breaking open of the cells can be advantageously supported and improved.

As an alternative or in addition to the resuspension of the microparticles by flow forces, it is possible for the resuspension of the microparticles to be supported by coupling further mechanical energy, for example ultrasound or shock waves, into the chamber. This has the advantage of intensifying the mechanical agitation of the microparticles and thus the lysis action.

In a further embodiment, the method can comprise a step of filling or flushing the microparticles across the inlet opening into the chamber and/or of packing the microparticles in the tapered section of the chamber. This has the advantage of being able to achieve an especially dense packing of the microparticles, increasing the efficiency of the accumulation of the organic cells. More particularly, it is thus possible, for example after transport of the system, during which the packing of the microparticles has become loose possibly as a result of acting impacts or vibrations, to achieve a renewed dense packing of the microparticles. A further advantage is that the chamber can be used for other purposes in preceding process steps, for example as reaction chamber or prestorage chamber. The microparticles are then flushed in only when required. Furthermore, it is thus possible for a chamber-comprising element of the microfluidic system and the stationary phase to be provided independently and thus for an area of application of the microfluidic system to be advantageously broadened, by it being possible for the microfluidic system to be, for example, organized and adapted in a customer-specific manner. The microparticles can be filled in or flushed in by, for example, the microparticles in a mobile phase, for example water or an aqueous buffer, being pumped or pipetted into the chamber. The microparticles can be packed by, for example, sedimentation due to gravity or pumping or flushing a liquid across the microparticles, and the flow direction in this connection is directed from the first opening of the chamber across the (more particularly tapering) section and the filter into the second opening. If a pump is used, this can be situated upstream or downstream of the chamber, and so the liquid is either pumped with positive pressure across the microparticles or sucked with negative pressure.

Furthermore, the method can comprise a step of introducing a binder, for example a binding buffer, into the chamber. This makes it possible for nucleic acids released from the cells on the basis of the disruption to be bound to the microparticles, for example by means of electrostatic interactions. With this embodiment of the method, a further treatment of the released nucleic acids, such as, for example, a wash or an accumulation on the microparticles, can be readily prepared.

Furthermore, the method can comprise a step of packing the microparticles having the nucleic acids bound to the microparticles in the tapered section of the chamber. With this embodiment, it is possible to carry out a concentration of the nucleic acids to a very small space and thus an elution of the nucleic acids from a very small volume. In said step, the packing can, for example, occur by the liquid present in the chamber or the binder being sucked off via the second opening.

To achieve an especially good purity of the nucleic acids, it is possible, following the step of introducing the binder, to carry out a wash of the microparticles. A wash can, for example, be carried out by guiding a wash buffer across the microparticles. In this step too, the wash buffer can be guided into the chamber in such a way that a resuspension of the microparticles takes place, for example by flushing in across the second opening. This has the advantage of contamination being especially effectively flushed out.

The method can comprise a step of eluting the nucleic acids from the microparticles and of transporting the nucleic acids from the chamber through the filter and the second opening. Said step can be carried out by, for example, flushing through the first or second opening water and/or an eluent across the nucleic acids accumulated before the filter. For example, the eluent can be flushed into the chamber across the second opening, incubated for a certain period, and then sucked off again through the second opening. This embodiment ensures, in a rapid and simple manner, a separation of the tested substance from the agents for making said substance available. Optionally, the chamber can also be heated during the elution, for example to temperatures between 30 and 70° C.

Before the step of eluting the nucleic acids, the method can comprise a step of drying the microparticles and the filter. This has the advantage of residues of the binder being especially efficiently removed and thus of a more complete elution being possible. The drying can, for example, be achieved by flushing air or nitrogen across the microparticles and/or by heating the chamber, for example to temperatures between 40 and 70° C.

In a further embodiment, the method can comprise a step of introducing a cleaning agent, for example a wash buffer, into the chamber in order to clean the organic cells. Said step can be carried out after the step of accumulating the organic cells in the tapered section of the chamber. This method step generally improves the purity of the sample; more particularly, substances interfering with subsequent process steps are removed. In this case, the cleaning agent is advantageously introduced through the first opening in order not to interfere with the packing of the microparticles and in order to avoid accumulated cells being flushed out of the chamber and thus being lost.

Furthermore, a microfluidic system for processing organic cells is presented, wherein the microfluidic system comprises the following features:

a chamber for accommodating a stationary phase present in the form of a plurality of microparticles and a mobile phase comprising a plurality of organic cells, wherein the chamber comprises a (more particularly tapered) section suitable for an accumulation of the microparticles and/or the organic cells;

a first opening coupled to the chamber for letting the microparticles and/or the organic cells into the chamber;

a filter which is downstream of the (more particularly tapered) section of the chamber and impermeable at least to the microparticles; and a second opening which is downstream of the filter and coupled to the chamber.

The microfluidic system can be understood to mean a device which is operated using liquids and/or gases in a very small space. The chamber can have an elongated shape, wherein the first opening can be arranged on a short side of the chamber. The tapered section of the chamber can be a region of the trough-shaped chamber having a smaller depth than a main section of the trough-shaped chamber. The tapered gap can be formed at a maximum distance from the first opening. The first opening can generally be referred to as an inlet opening into the chamber and the second opening can generally be referred to as an outlet opening from the chamber. The placement of the filter downstream of the tapered section and the placement of the second opening downstream of the filter can be understood as being set in relation to a position of the chamber. The placement of the filter downstream of the tapered section and the placement of the second opening downstream of the filter can also be understood to be in relation to a fundamental function of the microfluidic system, according to which a substance to be tested is fed to the microfluidic system across the first opening at the start of the above-described method of processing organic cells and is removed from the microfluidic system across the second opening at the end of the method. The tapered section and also the second opening of the chamber can be situated, with regard to gravity, at the lower end of the chamber, and so the microparticles sediment in the tapered section in the absence of a stream. The first opening can be situated at the upper end, with regard to gravity, of the chamber. This has the advantage that, when flushing liquids into the chamber across the second opening, air present in the chamber can escape across the first opening. In one variant of the system, this venting function can also be performed by a further, third opening. Advantageously, the chamber region opposing the filter and intended for accommodating the packing of microparticles is configured in such a way that there are no fluidically "dead" corners, i.e. regions which, when flushing liquids across the microparticles, are not subjected to flow-through or are only poorly subjected to flow-through. To this end, the lower end, with regard to gravity, of the chamber can run in a slanting manner or in a rounded manner toward the filter. More particularly, in this connection, the base of the chamber can be adapted to the shape of the filter in such a way that no subregion of the chamber is, with regard to gravity, deeper than the lowest end of the filter.

In one embodiment, a wall of the chamber of the microfluidic system or a subregion of the same, for example a circular subregion, can be elastic, more particularly formed as a membrane. The wall is thereby suited to transferring shock waves or ultrasonic pulses to a content of the chamber. Thus, it is easily possible, by means of additional mechanical agitation, to exert an additional grinding action and/or lysis action on the organic cells.

More particularly, the microfluidic system can be formed as a layer system composed of at least one base element and one lid element for covering the base element. In this connection, the chamber can be created in a trough-shaped manner in the base element and the first opening can be part of a first channel passing through the base element and the filter can be arranged in a region of the lid element that is opposite to the tapered section of the chamber. In this modular form, the microfluidic system can be produced especially rapidly and cost-effectively and readily adapted according to customer wishes.

In one embodiment, the filter can be arranged on a main side of the lid element that is facing the chamber and the second opening can be part of a second channel adjacent to the filter and passing through the lid element. In this embodiment, the microfluidic system can be advantageously realized with a small installation space.

Alternatively, the microfluidic system can be characterized in that the filter is arranged on a further main side of the lid element that is facing away from the chamber and is coupled to the chamber via a connecting channel created in the lid element. The second opening can then be part of a second channel adjacent to the filter, which channel passes through a cover element covering the lid element. This embodiment ensures an advantageous, more uniform flow of the substances to be tested on the filter.

Furthermore, the chamber can be divided into a lysis chamber coupled to the first opening and a filter chamber comprising the tapered section. The lysis chamber and the filter chamber can be connected via a passage channel. This embodiment has the advantage that the filtering of the substances to be tested can be carried out at a further distance from the lysis of the organic cells containing them, and this can advantageously maximize a concentration of the substances to be tested.

In a further embodiment of the microfluidic system, the chamber can have a tube shape. In this connection, the filter can form a base of the chamber. Said embodiment can also allow a more homogeneous flow onto the filter by the substances to be tested.

Furthermore, a manufacturing method for producing a microfluidic system for processing organic cells is presented, wherein the manufacturing method comprises the following steps:

providing a base element in which a chamber is created in a trough-shaped manner and which comprises a first opening which is part of a first channel passing through the base element;

providing a lid element;

providing a filter in the base element or lid element; and fitting the lid element on the base element in such a way that the filter is arranged adjacent to a (more particularly tapered) section of the chamber.

Also by means of this variant embodiment of the disclosure in the form of a manufacturing method, it is possible to rapidly and efficiently achieve the object underlying the disclosure.

BRIEF DESCRIPTION OF THE DRAWINGS

The approach presented here will now be more particularly elucidated by way of example with reference to the attached drawings in which:

FIGS. 6 to 11 show phase diagrams to illustrate a manner of functioning of the microfluidic system from FIG. 2, according to one exemplary embodiment of the present disclosure;

In the following description of favorable exemplary embodiments of the present disclosure, the same or similar reference signs are used for the elements which are shown in the various figures and act similarly, wherein a repeated description of said elements is dispensed with.

DETAILED DESCRIPTION

Figure 1:
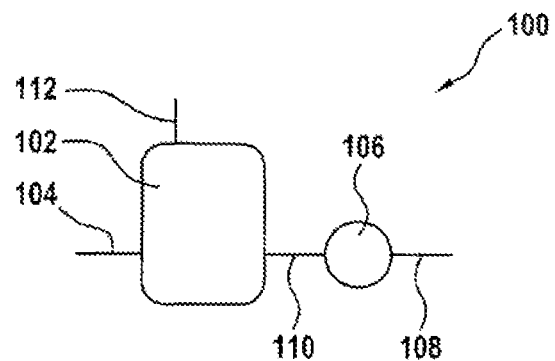
FIG. 1 shows a block diagram of a microfluidic system for processing organic cells, according to one exemplary embodiment of the present disclosure.

FIG. 1 shows a block diagram of one exemplary embodiment of a microfluidic system 100 for processing organic cells. The microfluidic system 100 is used for processing organic cells using microparticles and comprises a chamber 102, a first channel 104, a filter 106 and a second channel 108. In this connection, the first channel 104 forms an inlet channel for letting microparticles and/or a sample containing organic cells into the chamber 102. The second channel 108 contacts a reverse side of the filter or filter element 106 and forms an outlet channel for letting out from the microfluidic system 100 a substance broken out of the organic cells by means of the microparticles and the lysis agent and purified by means of the packing of microparticles. The chamber 102 and the filter element 106 are connected fluidically via a connecting channel 110, it also being possible for the connecting channel to be omitted or to be part of the chamber. In the exemplary embodiment shown in FIG. 1, the microfluidic system 100 is additionally provided with a venting channel 112 for venting the chamber 102. A volume of the chamber 102, in which lysis and purification of the sample take place, is between, for example, 100 microliters and 10 milliliters, typically about two milliliters. The filter element 106 is, for example, in the form of a plastic frit, a porous plastic support, a perforated membrane, a rake-type arrangement of columns or a metal mesh. For example, the filter element can also be implemented as a silicon structural component, for example having a perforated membrane or a channel piece interrupted in a rake-type manner by small columns. In this connection, the perforations, pores or columns preferably have a width or a gap of less than 100 micrometers.

Figure 2:
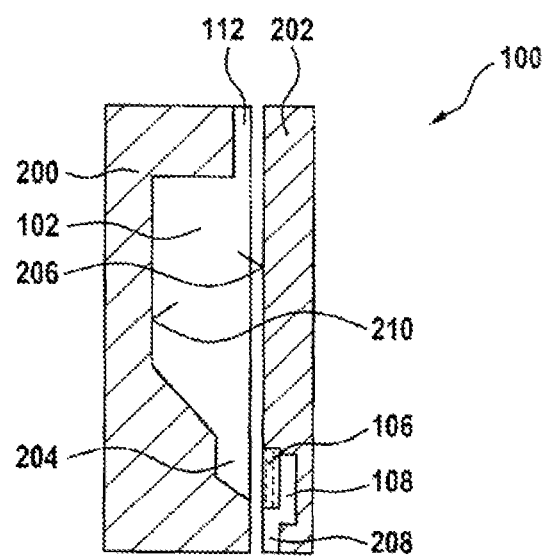
FIG. 2 shows a sectional view of a microfluidic system according to one exemplary embodiment of the present disclosure.

FIG. 2 shows a sectional view of the microfluidic system 100 presented in FIG. 1 by means of a block diagram, according to one exemplary embodiment of the present disclosure. As shown by the diagram in FIG. 2, the exemplary microfluidic system 100 is realized as a polymeric multilayer structure and consists of a base element 200 and a lid element 202, with the base element 200 having a greater thickness than the lid element 202. The chamber 102 is created in the base element 200 and comprises at one end a taper 204, which makes it possible for liquids to be completely removed from the chamber 102. This is achieved by the second opening being situated on the lowest end, with regard to gravity, of the taper. The filter element 106 is arranged in the lid element 202 directly opposite to the taper 204. The connecting channel shown in FIG. 1 by means of the block diagram is therefore omitted in the exemplary embodiment of the microfluidic system 100 that is shown in FIG. 2, the advantage of this being that a dead volume is reduced and a problem of clogging of the connecting channel is avoided. In the exemplary embodiment shown in FIG. 2, the filter element 106 is pressed into the lid element 202 in order to achieve a lateral sealing of the filter element 106. The dimensions of the chamber are advantageously greater than about 3 millimeters in each spatial direction. The advantage of this is that air bubbles present in the chamber or arising upon introduction of liquids into the chamber rise to the top and are removed from the system.

In the diagram in FIG. 2, the microfluidic layer system 100 is shown in a positioning during operation and thus standing on one lateral face, i.e. the base element 200 is now situated to the side of the lid element 202. As shown by the diagram in FIG. 2, the chamber 102 is created in the base element 200 in the form of a trough. The taper 204 is formed at one end of the trough by inclinations in the material of the base element 200, with the inclinations proceeding in such a way that, in the position of the microfluidic system 100 that is shown in FIG. 2, any moving material introduced into the chamber 102, for example the phases used in an analysis, is collected in the tapered section 204 opposite to the filter 106. In the exemplary embodiment of the microfluidic system 100 that is shown in FIG. 2, the filter 106 is arranged at a main side 206 of the lid element 202 that is facing the chamber 102.

The first channel 112 for charging the chamber 102 with a sample to be analyzed forms a first opening of the microfluidic system 100. The second channel 108 adjacent to the filter 106 passes through the lid element 202 comprises a second opening 208, across which liquids can be removed from the microfluidic system 100. The second channel or outlet channel 108 extends downward substantially parallel to the taper 204 in the figure, and so substances to be tested can be easily removed from the microfluidic system 100.

Figure 3:
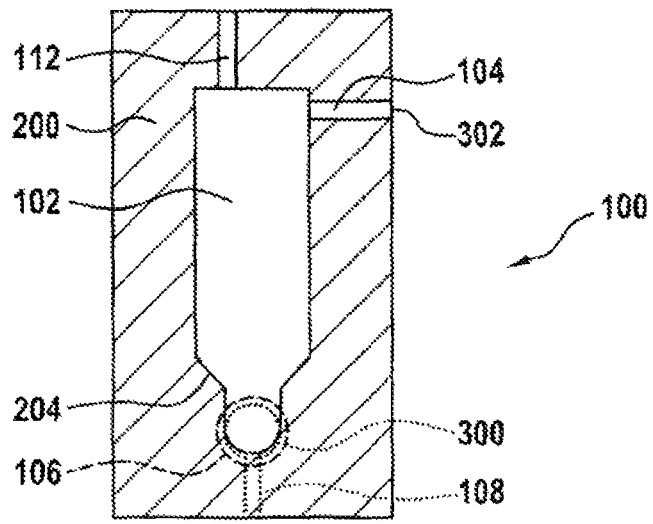
FIG. 3 shows a further sectional view of the microfluidic system from FIG. 2.

FIG. 3 shows the exemplary microfluidic system 100 from FIG. 2 by means of a longitudinal section through the base element 200. A transverse section of the filter 106 downstream, in this view, of the tapered section 204 of the chamber 102 is indicated by a circular broken line. The second channel 108 downstream, in this view, of the filter 106 is indicated by a dotted line. A transverse section of an outlet 300 of the second channel 108 that is adjacent to the filter element 106 is indicated by a circular broken line. The diagram in FIG. 3 thus clearly shows that a diameter of the filter element 106 is somewhat larger, for example from 0.5 to 2 millimeter larger, than a width of the taper 204. This measure of making the filter 106 wider than the taper 204 ensures a better and more even flow onto the filter 106 and also a better sealing of the crossover between chamber 102 and filter 106. The reverse side of the filter element 106 is contacted by the second channel or draining channel 108.

The longitudinal sectional view of the exemplary microfluidic system 100 in FIG. 3 clearly shows that the first channel 104 passing transversely through the base element 200 comprises a first opening 302 for letting a sample and/or a plurality of microparticles into the chamber 102. Furthermore, the diagram in FIG. 3 clearly shows that, in the exemplary embodiment shown of the microfluidic system 100, the tapered section 204 is at a maximum distance from the first opening 302.

Figure 4:
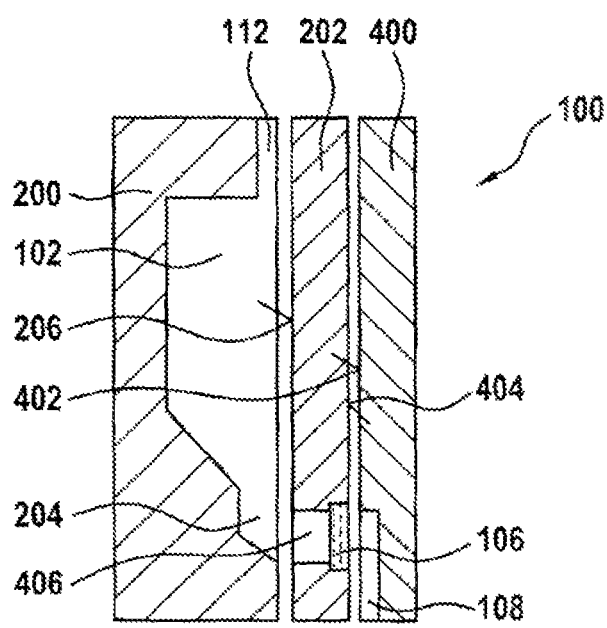
FIG. 4 shows a sectional view of a microfluidic system according to a further exemplary embodiment of the present disclosure.

FIG. 4 shows in turn, in a sectional view, a further exemplary embodiment of the microfluidic system 100. In this exemplary embodiment, the layer system composed of base element 200 and lid element 202 is expanded by a cover element 400. The cover element 400 has a thickness corresponding to the lid element 202 and is arranged on the lid element 202. More particularly, in the exemplary embodiment shown in FIG. 4, the second channel 108 is created in the cover element 400, specifically on a main side 402 of the cover element 400 that is facing the lid element 202. In contrast to the exemplary embodiment presented in FIGS. 2 and 3, the filter element 106 is arranged in a further main side 404 of the lid element 202 that is opposite to the main side 206 and is facing away from the base element 200 comprising the chamber 102, and is coupled to the chamber 102 via a connecting channel 406 passing transversely through the lid element 202.

The alternative implementation of the microfluidic system 100 that is shown in FIG. 4, in which implementation the filter element 106 is positioned on the reverse side 404 of the lid element 202, offers the advantage that a more homogeneous flow onto the filter element 106 is achieved and the filter element 106 is even better sealed laterally. The further lid or the cover element 400 seals the structure composed of base element 200 and lid element 202.

In further exemplary embodiments, which are not shown in the figures, the chamber 102 is divided into a lysis chamber coupled to the first opening 302 and a filter chamber comprising the tapered section 204. For the fluidic coupling, the lysis chamber and the filter chamber can be connected via a passage channel. The advantage of this implementation is that the filter element 106 can also be positioned at a greater distance from the lysis chamber. Furthermore, the chamber 102 can be implemented as a tube and can be, in its main extent transverse to the main side 206 of the lid element 202, created in the base element 200. The filter element 106 can then form a base of the chamber 102. The advantage of this exemplary implementation is that a more homogeneous flow onto the filter element 106 is achieved. The tube can, for example, be adhesively bonded or welded onto the multilayer structure.

Figure 5:
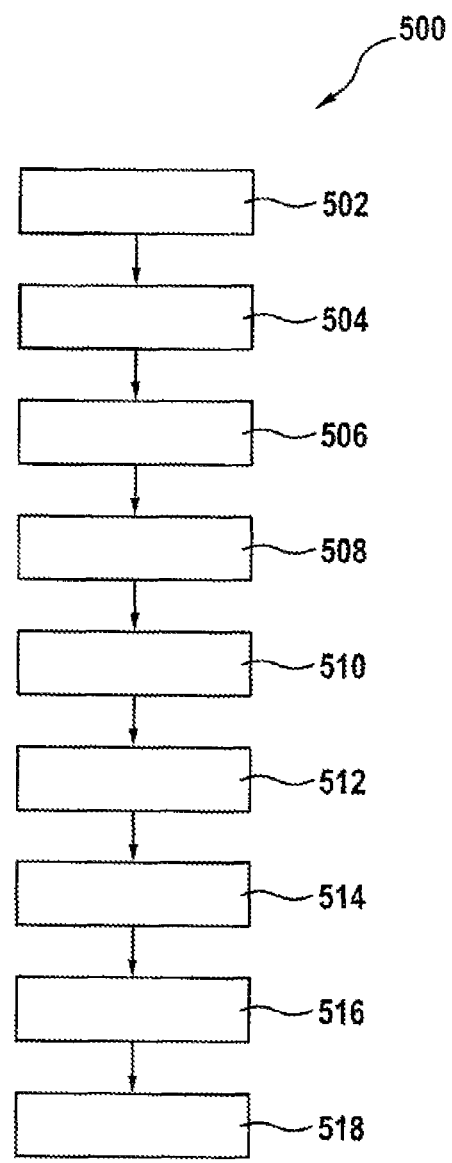
FIG. 5 shows a flowchart of a method for processing organic cells, according to one exemplary embodiment of the present disclosure.

FIG. 5 shows a flowchart of one exemplary embodiment of a method 500 for processing organic cells from a sample. The method 500 can be carried out a microfluidic system presented by means of FIGS. 1 to 4.

In a step 502, microparticles, for example small beads having a diameter in the micrometer range, are filled or flushed across an inlet opening of a microfluidic system carrying out the method 500 into a chamber of the microfluidic system and packed in a tapered section of the chamber before a filter impermeable to the microparticles and organic cells.

In a step 504, there is provided the microfluidic system containing the plurality of microparticles packed in the tapered section of the chamber, and so in a step 506, a sample containing a plurality of organic cells can be let in across the first opening into the chamber of the microfluidic system.

In a step 508, the organic cells are accumulated in the tapered section on the microparticles packed therein. The sample comprising the organic cells can be understood to mean a mobile phase containing the organic cells. The microparticles can be understood to mean a stationary phase of the microfluidic system carrying out the method. The stationary phase is configured to enter into an interaction with the mobile phase of the microfluidic system in order to process the organic cells for a subsequent analysis, for example by a DNA or RNA present in the organic cells being lysed from the cells, optionally in combination with the lysis agent. During the accumulation, the microparticles are continuously pressed against the filter by the prevailing flow, and as a result, a steady packing density can be maintained or the packing density can even be increased even further. This further improves the efficiency of the accumulation.

The steps of letting-in 506 and of accumulation 508 can also take place simultaneously by the sample being continuously flushed from the first opening of the chamber across the microparticles.

In one exemplary embodiment of the method 500, the steps 502 to 508 can be carried out simultaneously or in an altered sequence. For example, the microparticles are added to the sample and flushed together with said sample into the system, and so a packing of the microparticles and an accumulation of organic cells on this packing take place simultaneously. This has the advantage of saving process steps and liquids and of being able to implement the method or system in a more rapid and more greatly space-saving manner. In a further exemplary embodiment, the method 500 can start with the step of providing the microfluidic system comprising the plurality of microparticles. This means that, for example, the microparticles are already filled into the system in a production facility.

In a step 510, a cleaning agent is introduced into the chamber across a first opening of the microfluidic system in order to clean the microparticles and the organic cells. The step 510 is optional and can, according to exemplary embodiments, be repeated at further points in the method 500. In a step 512 of the method 500, a lysis agent is flushed into the chamber in order to achieve a disruption of the organic cells and release of nucleic acids present in the cells. More particularly, in the step 512, the lysis agent is flushed into the chamber across the second opening of the microfluidic system that is downstream of the filter, and as a result, the microparticles and organic cells are resuspended. In a step 514, a binder is introduced into the chamber in order for the nucleic acids released from the cells on the basis of the disruption to bind to the microparticles. In this case, an introduction of the binder into the chamber across the second opening downstream of the filter allows an especially good mixing with the liquid already present in the chamber and an efficient washing around the microparticles. The step 514 can optionally be followed by a step of washing the microparticles and the nucleic acids adsorbed to the microparticles.

In a step 516, the microparticles or beads having the nucleic acids bound to the microparticles are packed in the tapered section of the chamber. In a step 518, the nucleic acids are eluted from the microparticles and transported from the microfluidic system through the filter and the second opening for a subsequent analysis.

FIGS. 6 to 11 show phase diagrams of one exemplary embodiment of the method for processing organic cells from a sample, as presented by means of FIG. 5, for the purpose of clearly illustrating a manner of functioning of the microfluidic system 100 carrying out the method.

Figure 6:
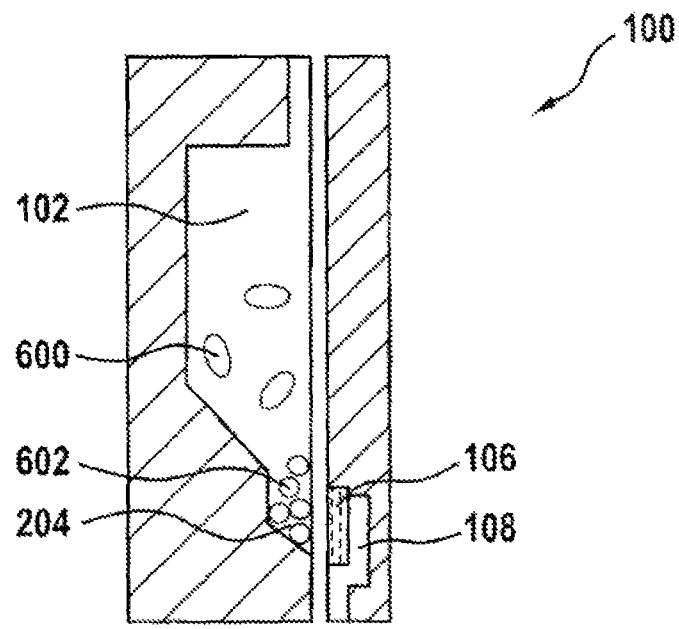

FIG. 6 illustrates the method step of letting a sample comprising a plurality of organic cells 600 into the chamber 102 across the first opening (which is formed by the channel at the upper end of the chamber) of the microfluidic system 100 or an early phase in the step of accumulating the organic cells, in which phase cells are still situated in the region before the microparticles. The sample can have a volume between 50 microliters and 20 milliliters. The sample can be a body fluid such as, for example, blood, urine, sputum, be a lavage fluid, a rinsed-out swab or a liquefied tissue sample or else be a cell suspension from a culture. In the step of letting-in, the sample containing the organic cells 600 is pumped or sucked through the inlet channel and the chamber 102 in the direction of the outlet channel 108. For this purpose, it is possible, for example, to use peristaltic or membrane pumps. It is also possible for the flushing to be carried out manually, for example by pipetting or using a syringe. More particularly, the system shown can be part of a larger microfluidic system which also comprises microfluidic pumps, for example a microfluidic membrane pump, and also chambers, for example for sample input. The pump can be situated upstream or downstream of the chamber.

Microparticles or beads 602 are already introduced into the chamber 102 and packed to form a bed before the filter element 106 in the tapered section 204 of the chamber 102. According to exemplary embodiments, this packing of the bed can already take place during the production of the system 100 or just before an analysis of a sample or just before letting in a sample, for example by flushing in the microparticles 602, or during the analysis, for example by the microparticles 602 being pushed together to form a packing while the sample is being let in. The filter element 106 is configured such that the microparticles 602 are retained. The microparticles 602 can, for example, be in the form of silica beads or particles having a diameter between 10 micrometers and 1 millimeter. Advantageously, the packed microparticles completely cover the filter element. This avoids the formation of a bypass past the packed microparticles, through which organic cells might be lost.

Figure 7:
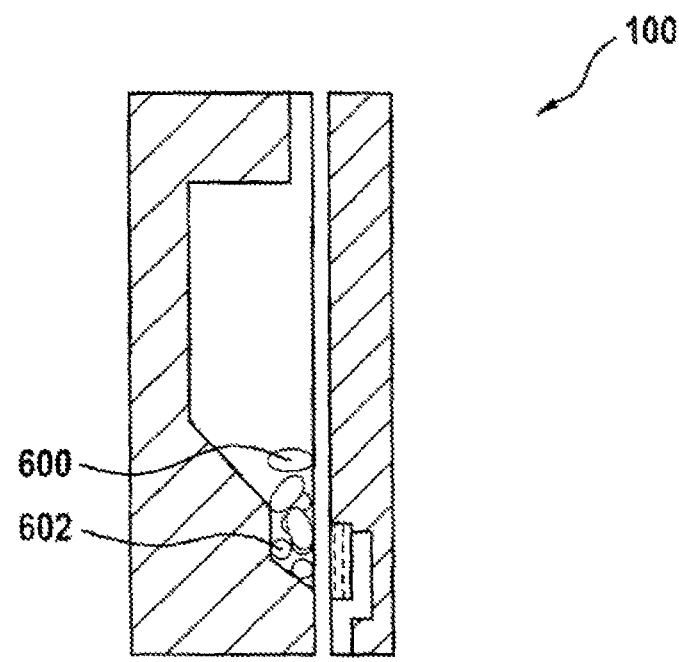

FIG. 7 shows by means of a further phase diagram how the cells 600 present in the sample, for example human cells, bacteria or fungi, are retained on the bed of microparticles 602 and thus accumulated. What is shown is the state in which the cells 600 are situated on the bed, for example toward the end of the accumulation.

FIG. 8 shows a phase diagram of the method stage of resuspending the organic cells 600 and microparticles 602. As shown by the diagram in FIG. 8, the microparticles 602 and accumulated cells 602 are resuspended or swirled using a lysis agent or lysis buffer from the tapered section 204 into the chamber volume 102. In the exemplary embodiment shown in FIG. 8, the resuspension is achieved by the lysis buffer being pumped from the outlet channel 108 into the chamber 102. However, the resuspension can in principle also be achieved by flushing in the lysis buffer through a further channel which opens into the region of the chamber in which the microparticles are situated. During this action, air present in the chamber escapes across the inlet channel or the venting channel. The lysis buffer remains in contact with the cells over an incubation time, for example between 1 and 30 minutes, and brings about a disruption of the cells 600, releasing nucleic acids 800, for example DNA, present in the cells 600. To this end, the lysis buffer can contain enzymes, for example lysozyme and/or proteinases, and/or chemical lysis reagents, for example detergents or chaotropic or basic components. In this case, the effect of the resuspension of the microparticles is that a good mixing of cells and lysis buffer is achieved, a homogeneous concentration distribution of the lysis agent, for example the enzymes, is attained in the chamber, and the lysis buffer reaches all the cells. In addition, a resuspension of the microparticles supports the lysis through an exertion of mechanical forces on the cells. In the simplest case, the microparticles are resuspended by flow forces.

During the lysis, the chamber can be heated, for example to temperatures between 30 and 60° C. This has the advantage that chemical reactions generally proceed more rapidly and, in particular, enzymes possibly used for the lysis have a higher activity. A heating of the chamber to higher temperatures, for example between 90 and 97° C., may also be meaningful. In this case, a thermal lysis substantially takes place.

In one exemplary embodiment, the movement of the microparticles can be kept going during the lysis by pumping air, continuously or in spurts, from the outlet channel 108 into the chamber 102. This can achieve a continuous agitation of the microparticles. This has the advantage of exerting mechanical forces onto the organic cells over the entire incubation time. Easy-to-lyse cells may thus possibly be lysed by mechanical forces alone.

In further exemplary embodiments, the resuspension of the microparticles 602 and cells 600 can be supported by shock waves or ultrasonic pulses. In this case, a wall 210 of the chamber 102 is completely or partly implemented as a membrane through which the shock waves or the ultrasonic pulses are coupled in. To this end, the membrane is contacted with an injector or ultrasonic horn. This also has the advantage that an even stronger grinding action and thus lysis action on the cells 600 is achieved by the direct mechanical agitation of the microparticles 602, possibly also by cavitation. It may thus even be possible to completely dispense with the addition of, for example, enzymes or chemical lysis reagents in the lysis buffer and, in the simplest case, to use water or an aqueous buffer as lysis agent. A liquid arising during this process step is called lysate.

The phase diagram shown in FIG. 9 illustrates the method step of introducing a binder or binding buffer, which is flushed into the chamber 102 from the outlet channel 108. In this case, the lysate is not displaced from the chamber 102, but is instead mixed with the binding buffer. This avoids lysate and thus nucleic acids present therein getting lost and no longer being available for the analysis. In one variant, the binding buffer can again be flushed into the chamber through a third channel, with the outlet channel remaining closed, so that no lysate escapes. The binding buffer brings about a binding of the nucleic acids 800 liberated from the cells to the microparticles 602. To this end, the binding buffer can contain alcohols, for example ethanol or isopropanol. The mixing of the binding buffer with the lysate can be supported by additionally flushing air into the chamber through the outlet channel.

Figure 10:
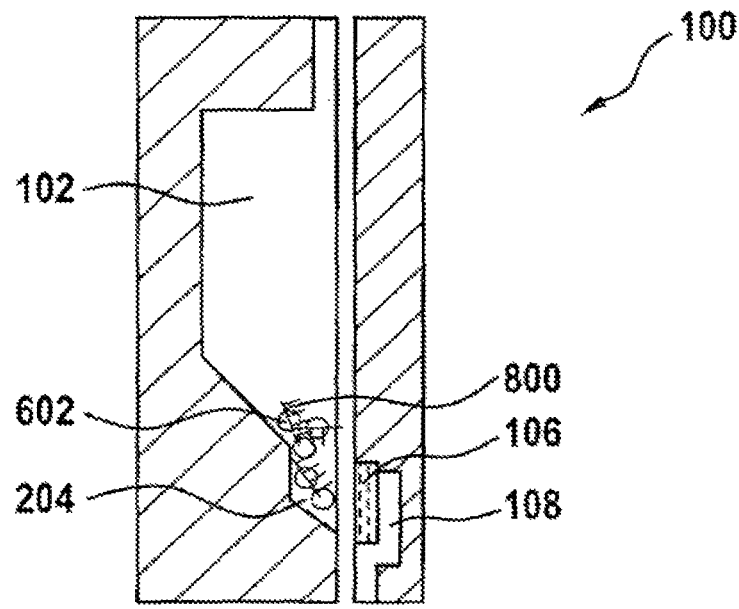

FIG. 10 shows a phase diagram to illustrate an accumulation of the microparticles 602 having the nucleic acids 800 bound thereto. The diagram shows how the mixture comprising microparticles 602 and nucleic acids 800, or the lysate mixed with binding buffer, is flushed from the chamber 102 in the direction of the outlet channel 108. In this case, the microparticles 602 having the adsorbed nucleic acids 800 are packed again in the tapered section 204 of the chamber 102 before the filter element 106 to form a bed. In this state, the microparticles 602 can, according to exemplary embodiments, be washed with a wash agent or wash buffer in order to remove cell residues, for example proteins. To this end, it is, for example, possible to pump a wash buffer into the chamber via the inlet channel and to pump it out therefrom via the outlet channel. Alternatively, a wash buffer can be pumped into the chamber via the outlet channel and then sucked off again via the outlet channel. The advantage of this is that the microparticles having the adsorbed nucleic acids are resuspended again and can thus be washed even more efficiently. The washing of the microparticles can also be carried out repeatedly.

Figure 11:
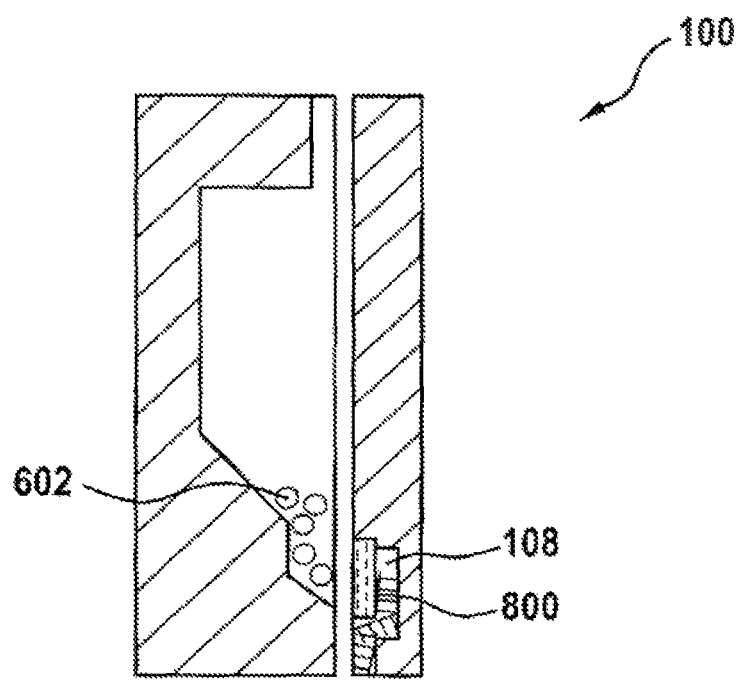

FIG. 11 illustrates by means of a further phase diagram the step according to the disclosure of eluting and transporting the nucleic acids 800 liberated from the cells. The nucleic acids 800 are eluted from the microparticles or beads 602 by flushing water or an elution buffer or eluent across the bed into the outlet channel 108.

In one variant of the method for processing organic cells from a sample, as presented by means of the phase diagrams shown in FIGS. 6 to 11, the method steps explained with reference to FIGS. 9, 10 and 11 are omitted. The lysate, possibly including the microparticles, is then firstly removed from the chamber 102, and the nucleic acids 800 are purified by, for example, being bound to a membrane, for example a silica membrane. This has the advantage that it is also possible to use microparticles 602 not suited to binding nucleic acids 800. The lysate can be removed from the chamber by, for example, pipetting or flushing through a further channel which opens into the chamber before the filter.

In a further variant of the method presented here, a digest of proteins present in the lysate is additionally carried out after the method step of resuspension that is illustrated by means of the diagram in FIG. 8. To this end, a buffer containing, for example, proteinase is flushed into the chamber 102 through the outlet channel 108, and mixed and incubated therein with the lysate. This has the advantage of removing impurities, for example proteins, even more effectively.

In a further variant of the method, it is possible in the steps of binding the nucleic acids to the microparticles, of washing the nucleic acids adsorbed to the microparticles and of elution for shock waves or ultrasonic energy to be briefly coupled into the chamber in each case. This may have the advantage of improving the resuspension of the beads in said steps and of thus improving the efficiency of the binding or washing or elution.

Furthermore, the microparticles and the filter can be dried before the step of eluting the nucleic acids.

Furthermore, in one exemplary embodiment of the method presented here, it is possible, after the method step of accumulating the cells 600 on the bed of microparticles 602 that is illustrated by means of the diagram in FIG. 7, to wash the accumulated cells 600, for example using a wash buffer or wash agent. This implementation of the method has the advantage that constituents of the sample which would interfere with the further purification and detection can be removed.

Furthermore, a preceding processing of the sample can be carried out before step I. For example, human cells present in the sample, for example blood cells, can be lysed by addition of proteinases or detergents or by osmotic shock or brief heating, for example to 70° C. During this action, bacteria or fungi present in the sample remain intact and can be accumulated on the bed in the following steps. As preceding processing, it is also possible to carry out a liquefaction of tissue constituents and a digest of proteins, for example by addition of proteinase.

In a further exemplary embodiment, a swab containing the sample can be rinsed out as a preceding processing in relation to the method step of letting the sample into the chamber 102 that is illustrated by means of the phase diagram in FIG. 6. The preceding processing has the advantage that the cells 600, the nucleic acid of which is to be detected, can be made better accessible to the purification.

In a further variant, silica-coated magnetic microparticles can be used. In the steps of lysis, of binding the nucleic acids to the microparticles, of washing the nucleic acids adsorbed to the microparticles and of elution, they can in each case be set in motion by means of an external magnetic field. This can improve the efficiency of the lysis or binding or washing or elution. The agitation of the microparticles by means of magnetic fields represents an alternative to the agitation of the microparticles by means of flow forces, shock waves or ultrasonic pulses. In this case, the use of magnetic fields may have, with respect to the use of shock waves or ultrasonic pulses, the advantage that mechanical access to an outer surface of the chamber is not required, and as a result, it may be possible to save installation space.

The method presented by means of the phase diagrams in FIGS. 6 to 11 allows the accumulation of pathogens from a sample, the subsequent lysis thereof and also the purification of the nucleic acid present, and is especially notable for the fact that, even in the case of an only low concentration of pathogens in a sample, a meaningful analysis of the pathogens can be allowed.

Figure 12:
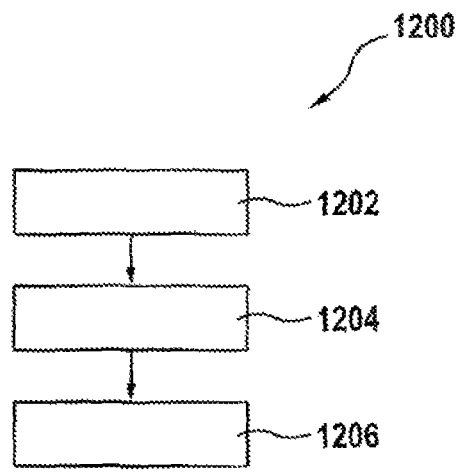
FIG. 12 shows a flowchart of a manufacturing method for producing a microfluidic system for processing organic cells, according to one exemplary embodiment of the present disclosure.

FIG. 12 shows a flowchart of one exemplary embodiment of a manufacturing method 1200 for producing a microfluidic system for processing organic cells. A microfluidic system produced by means of the manufacturing method 1200 can be one exemplary embodiment of the microfluidic system presented by means of the FIGS. 1 to 4.

In a step 1202, there is provided a base element having a chamber created in a trough-shaped manner in the base element, and a first channel coupled to the chamber and passing through the base element. In a step 1204, a lid element and a filter are provided. In a step 1206, the lid element is fitted onto the base element in such a way that the filter is arranged opposite or adjacent to a tapered section of the chamber.

Figure 13:
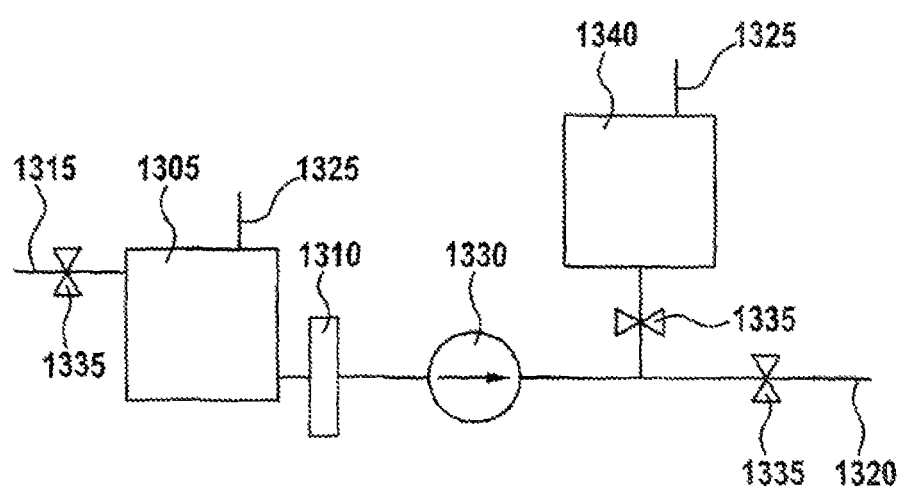
FIG. 13 shows a block diagram of a microfluidic system according to one exemplary embodiment of the present disclosure.

FIG. 13 shows a block diagram of an exemplary microfluidic system for carrying out the method according to the disclosure. Besides the chamber 1305 with filter 1310, inlet channel 1315, outlet channel 1320 and venting channel 1325, the system comprises a microfluidic pump 1330, microfluidic valves 1335 and further chambers 1340 (only one shown). The chambers 1340 serve as reservoirs for the storage of reagents, for example the lysis buffer, the binding buffer, the wash buffer and/or the elution buffer. Further reservoirs, for example for the storage of the sample, of liquids for flushing in the microparticles and of further wash buffers, can be connected to the inlet channel 1315. The chambers 1340 can likewise be vented by means of venting or ventilation channels 1325 in order to achieve a pressure equalization upon the removal of liquid from the chambers. The pump 1330 serves to flush the sample and possibly wash buffers via the inlet channel into the outlet channel. Furthermore, using the pump 1330, it is possible for lysis buffer, binding buffer and wash buffer to be flushed from the outlet into the chamber and sucked off again.

Figure 14:
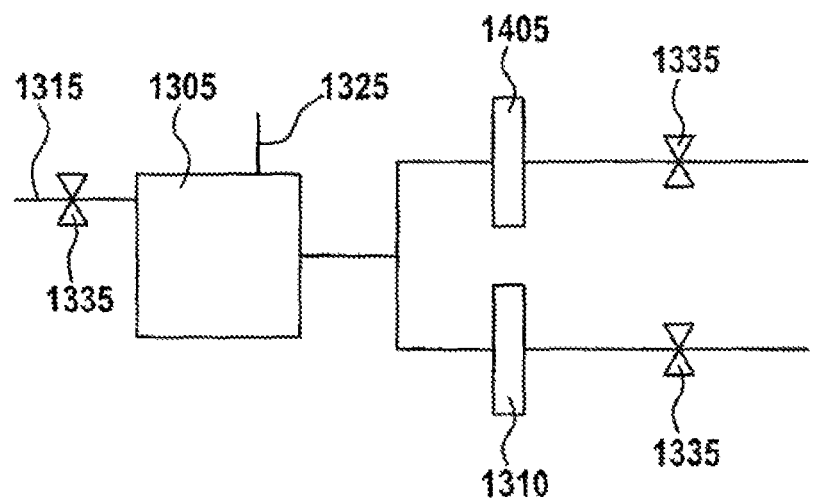
FIG. 14 shows a block diagram of a further microfluidic system according to one exemplary embodiment of the present disclosure.

FIG. 14 shows a block diagram of a topology of chamber 1305, filter 1310 and second opening in which a membrane 1405 suitable for purifying nucleic acids, for example a silica membrane, is connected parallel to the filter 1310. After the lysis, a switch is carried out from the path having filter 1310 to the path having the membrane 1405. During the pumping of the binding buffer/wash buffer for washing the nucleic acids/elution buffer, the microparticles are this time packed before the membrane 1405. The advantage of this is that the nucleic acids can be purified even more efficiently, especially in the case of a high load of nucleic acids, and/or microparticles not suitable for purifying nucleic acids can be used. Connecting channels between chamber and filter/membrane can again be omitted, i.e. the membrane 1405 can be directly arranged on the chamber 1305 just like filter 1310.

Figure 15A:
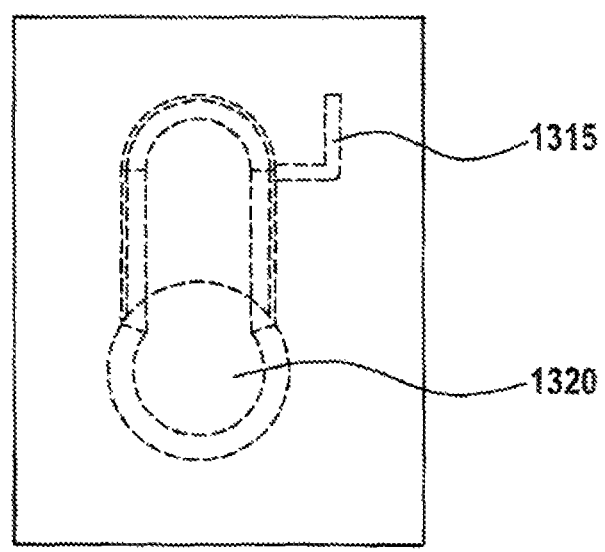
FIG. 15A shows a top view of components of a microfluidic system according to one exemplary embodiment of the present disclosure.
Figure 15B:
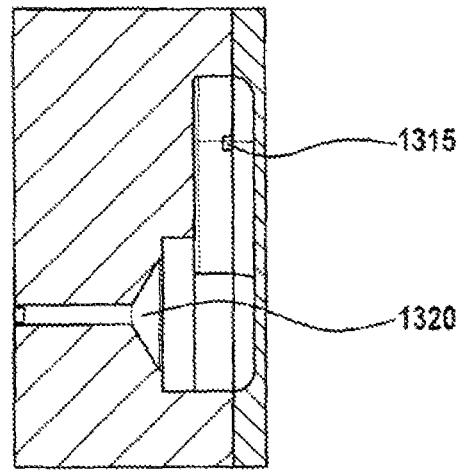
FIG. 15B shows a transverse sectional view of the components of the microfluidic system shown in FIG. 15A.
Figure 15C:
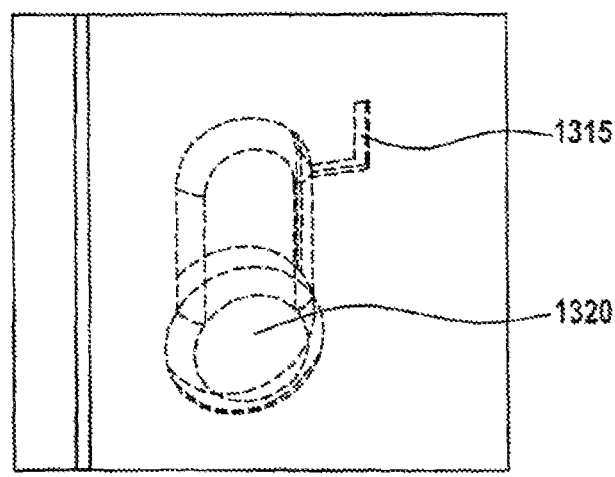
FIG. 15C shows a perspective view of the components of the microfluidic system shown in FIG. 15A.

The subfigures of FIG. 15 show a main part of the chamber 1305 and of the filter 1310 in one layer in top view (FIG. 15A), in transverse sectional view (FIG. 15B) and in perspective view (FIG. 15C). The inlet channel 1315 (wherein the further duct thereof is not shown) is shown laterally and the outlet channel 1320 is shown as a through-hole. The taper is omitted in the exemplary embodiment shown in the subfigures 15. A ventilation channel is not shown.

Figure 16A:
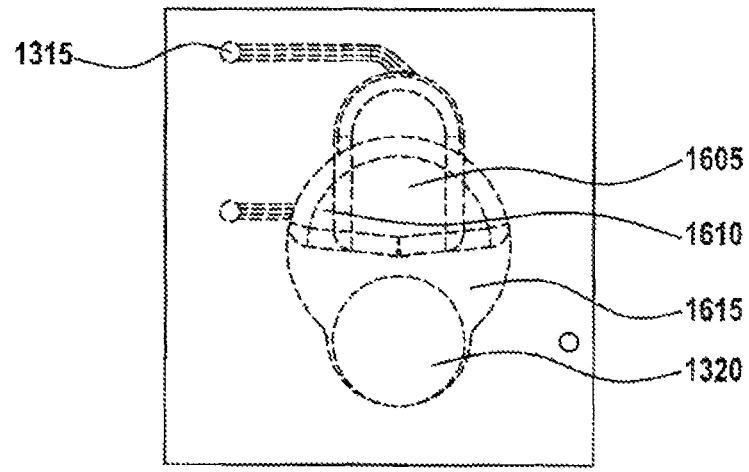
FIG. 16A shows a top view of further components of a microfluidic system according to one exemplary embodiment of the present disclosure.
Figure 16B:
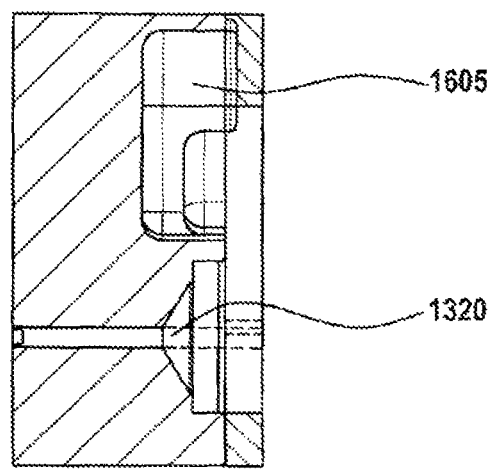
FIG. 16B shows a transverse sectional view of the components of the microfluidic system shown in FIG. 16A.
Figure 16C:
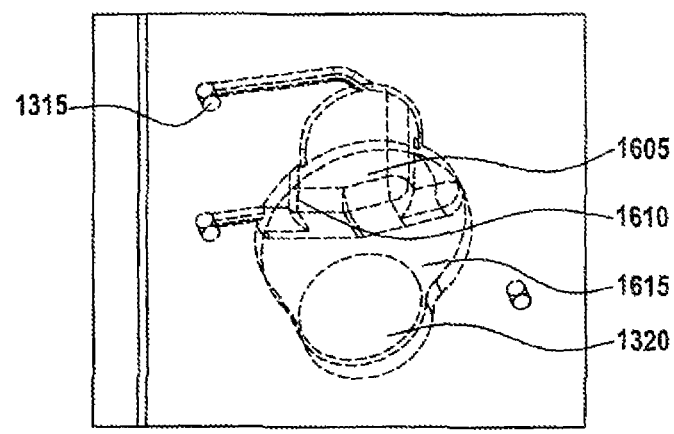
FIG. 16C shows a perspective view of the components of the microfluidic system shown in FIG. 16A.

The subfigures of FIG. 16 show a further depiction of a main part of the chamber 1305 and of the filter 1310 in different views (top view in FIG. 16A, transverse sectional view in FIG. 16B and perspective view in FIG. 16C). In this case, an additional expansion 1605 and through-hole 1610 are shown outwardly. The circular through-hole 1610 is capped by a further membrane 1615.

The concept presented herein for processing organic cells is, for example, useful in systems or laboratory routines which are used for diagnosing infectious diseases.

The exemplary embodiments which are described and which are shown in the figures are only selected by way of example. Different exemplary embodiments can be combined with one another in full or with respect to individual features. An exemplary embodiment can also be supplemented by features of a further exemplary embodiment.

Furthermore, the method steps presented here can be repeated and also carried out in an order different to the order described.

If an exemplary embodiment comprises an "and/or" linkage between a first feature and a second feature, this is to be read as meaning that the exemplary embodiment comprises, according to one embodiment, both the first feature and the second feature and, according to a further embodiment, either only the first feature or only the second feature.

What is claimed is:

1. A method for processing organic cells, comprising:
providing a microfluidic system having a chamber including a stationary phase in the form of a plurality of microparticles, the microfluidic system further including a filter that is impermeable to the microparticles, the filter having a first side arranged toward the chamber and an opposing second side;
letting a plurality of organic cells in a mobile phase into the chamber across a first opening of the microfluidic system;
accumulating the organic cells in a section of the chamber that is upstream of the filter; and
flushing a lysis agent through the filter from the second side toward the first side into the chamber to resuspend the microparticles and the organic cells in the chamber for a disruption of the organic cells causing a release of a nucleic acid from the organic cells in the chamber.

2. The method according to claim 1, wherein flushing the lysis agent into the chamber further includes flushing the lysis agent into the chamber across a second opening of the microfluidic system that is downstream of the filter.

3. The method according to claim 1, wherein, after flushing the lysis agent into the chamber, the microparticles are set into motion by coupling one of ultrasound and shockwaves into the chamber.

4. The method according to claim 1, further comprising at least one of (i) filling the microparticles across the first opening into the chamber, and (ii) packing the microparticles in a tapered section of the chamber.

5. The method according to claim 2, further comprising introducing a binder across the second opening into the chamber to enable a nucleic acid released from the cells on the basis of the disruption to bind to the microparticles.

6. The method according to claim 5, further comprising packing the microparticles having the nucleic acids bound to the microparticles in a tapered section of the chamber.

7. The method according to claim 5, further comprising eluting the nucleic acids from the microparticles and transporting the nucleic acid from the chamber through the filter and one of the second opening and a further opening.

8. The method according to claim 5, further comprising introducing a cleaning agent through the second opening into the chamber to clean the microparticles having the nucleic acids bound to the microparticles.

9. The method according to claim 1, wherein, after disrupting the organic cells, nucleic acids are purified on a separate membrane.

10. A method for processing organic cells, comprising:
providing a microfluidic system having a chamber including a stationary phase in the form of a plurality of microparticles, the microfluidic system further including a filter that is impermeable to the microparticles, the filter located in a channel, the filter having a first side arranged toward the chamber and an opposing second side; the channel comprising a second opening of the microfluidic system arranged between the chamber and the filter, the second opening in contact with the microparticles;
letting a plurality of organic cells in a mobile phase into the chamber across a first opening of the microfluidic system;
accumulating the organic cells in a section of the microfluidic system that is upstream of the filter; and
flushing a lysis agent in an upstream direction through the channel into the chamber, the channel arranged to allow the lysis agent to flow into the section of the chamber in which the microparticles are situated to resuspend the microparticles and the organic cells in the chamber for a disruption of the organic cells causing a release of nucleic acids from the organic cells in the chamber.

* * * * *